US005318009A

United States Patent [19]
Robinson

[11] Patent Number: 5,318,009
[45] Date of Patent: Jun. 7, 1994

[54] ILLUMINATED TONGUE DEPRESSOR

[75] Inventor: Herbert L. Robinson, Pompton Plains, N.J.

[73] Assignee: Scientific Medical Programs, Inc., Fairfield, N.J.

[21] Appl. No.: 25,649

[22] Filed: Mar. 3, 1993

[51] Int. Cl.$^5$ .............................................. A61B 1/06
[52] U.S. Cl. ...................................... 128/16; 128/23; 362/120; 362/157
[58] Field of Search .................................. 128/12–16, 128/10–11, 18, 22, 23; 362/32, 109, 120, 157, 276, 802; 433/140; 33/514, 511; D24/135, 136

[56] References Cited

U.S. PATENT DOCUMENTS

| D. 53,649 | 7/1919 | Weder et al. ....................... D24/136 |
| D. 217,410 | 4/1970 | Greatman ........................... D24/136 |
| 2,240,402 | 4/1941 | Joroslow . |
| 2,247,258 | 6/1941 | Shepard . |
| 2,723,661 | 11/1955 | Hull . |
| 3,195,536 | 7/1965 | Hovnanian et al. . |
| 3,349,764 | 10/1967 | Edinger et al. . |
| 3,734,084 | 5/1973 | Ousterhout . |
| 3,760,798 | 9/1973 | Edinger .............................. 128/16 |
| 3,890,960 | 6/1975 | Wunsch et al. . |
| 3,916,881 | 11/1975 | Heine . |
| 4,320,745 | 3/1982 | Bhitiyakul et al. . |
| 4,344,419 | 8/1982 | Burgin . |
| 4,517,964 | 5/1985 | Upsher . |
| 4,643,172 | 2/1987 | Taff et al. . |
| 4,807,599 | 2/1989 | Robinson et al. . |
| 4,936,171 | 6/1990 | Berg ................................... 362/120 |
| 4,996,976 | 3/1991 | Nakagawa . |
| 5,222,795 | 6/1993 | Hed .................................... 362/32 |

FOREIGN PATENT DOCUMENTS 339541 11/1989 European Pat. Off. ............. 128/11
252523 3/1912 Fed. Rep. of Germany ...... 362/157

Primary Examiner—Richard J. Apley
Assistant Examiner—Donna L. Maraglio
Attorney, Agent, or Firm—Sixbey, Friedman, Leedom & Ferguson

[57] ABSTRACT

The illuminated tongue depressor includes a handle having a battery-operated light source and a depressor blade selectively coupled with or uncoupled from the handle for discard and replacement. The blade includes a length extending longitudinally between a proximal end and a distal end and laterally between opposite sides, and includes upper and lower surfaces, a peripheral edge between the upper and lower surfaces defining a relatively thin blade thickness, a root adjacent the proximal end of the blade, a tip at the distal end of the blade, and a light conducting material between the upper and lower surfaces and extending along the blade from the root to at least a portion of the peripheral edge at the tip of the blade. A light directing configuration formed on the distal end directs the light transmitted by the light conducting material toward the area to be examined and includes an elevated portion at the tip and a support leg on both sides thereof for contacting the patient's tongue during use to maintain the elevated portion above the portion of the tongue immediately in front of the tip. The handle includes a movable arm and associated contact forming a switch which is automatically closed energizing the light source when the blade is moved into a coupled position, and automatically opened deenergizing the light source when the blade is moved to an uncoupled position.

16 Claims, 3 Drawing Sheets

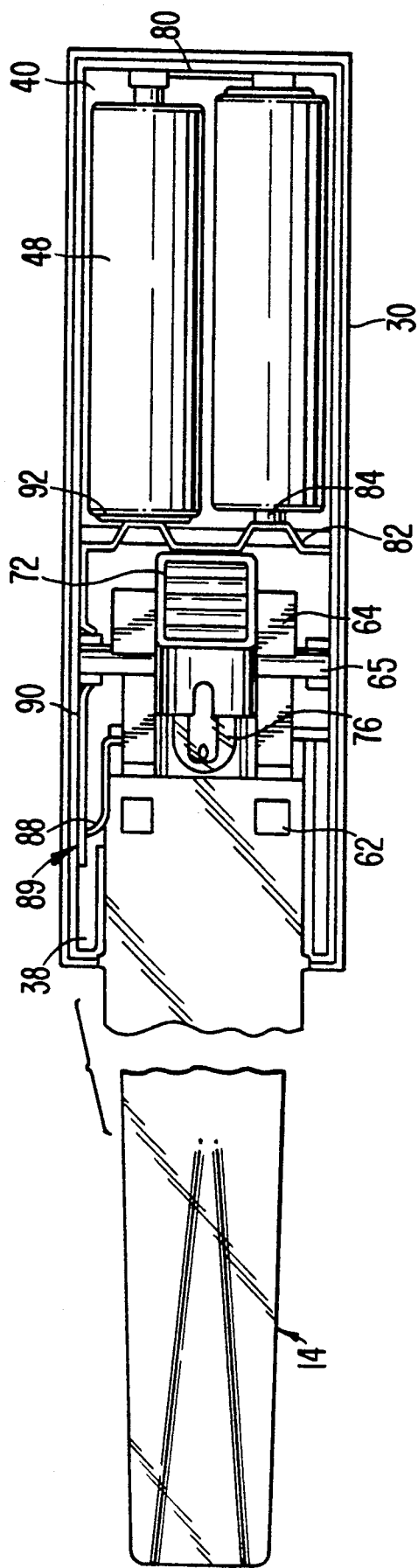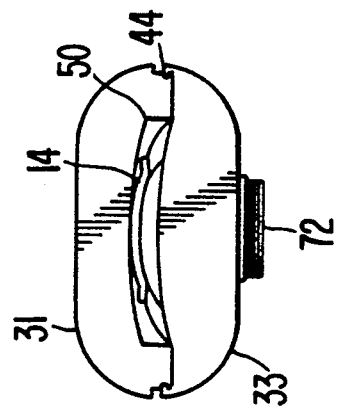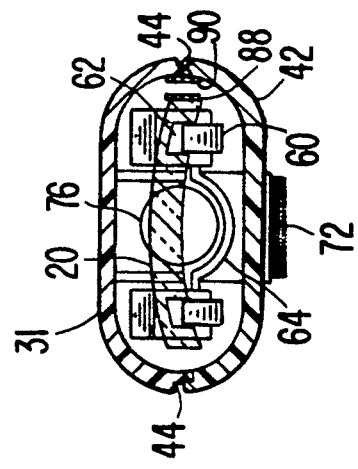

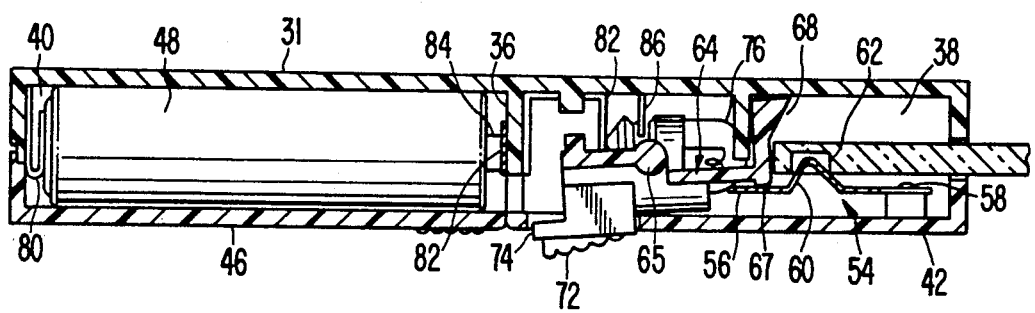
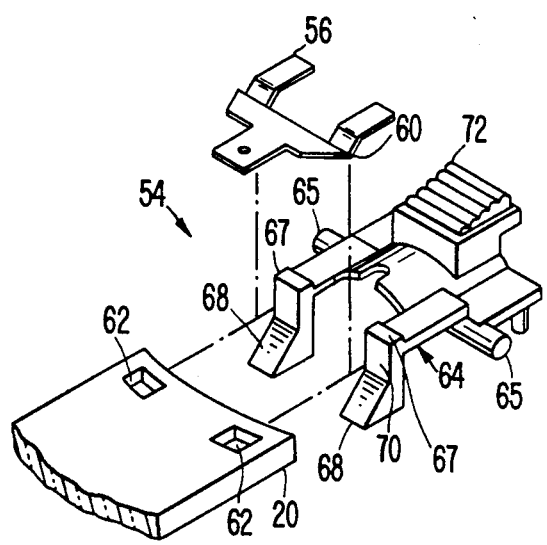
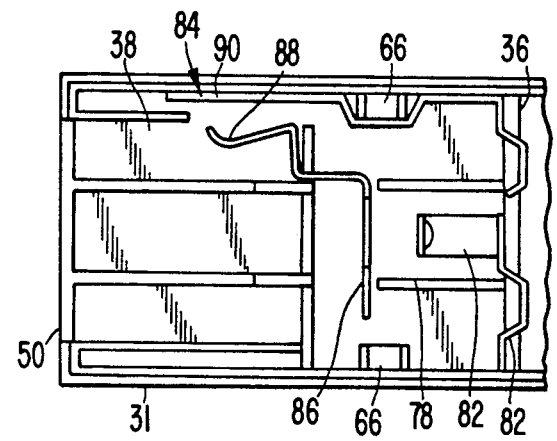
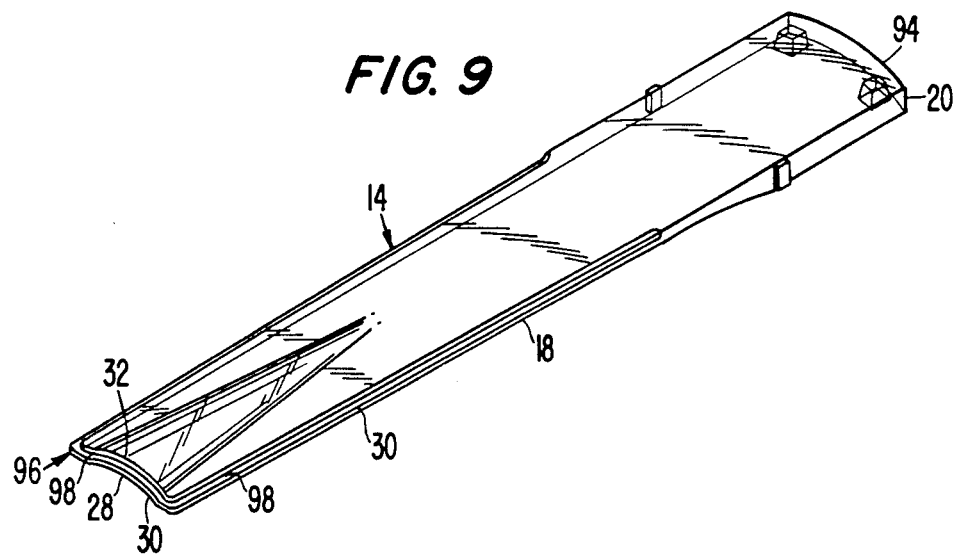

ILLUMINATED TONGUE DEPRESSOR

BACKGROUND OF THE INVENTION

The present invention relates generally to medical devices and pertains, more specifically, to a diagnostic spatula known more familiarly as a tongue depressor. In particular, the invention provides an improved tongue depressor which more effectively directs light to the area to be inspected aiding such inspection and facilitating examination.

Tongue depressors have been in use routinely in the examination of patients for a very long time. Despite efforts to develop and manufacture tongue depressors of other materials, by far the most commonly used tongue depressors are those constructed of wood. Suggestions for substituting a synthetic resin material for wood have been made but wood is still the preferred material and large numbers of wooden tongue depressors are consumed annually. In order to adequately inspect a patient's mouth and throat, the examiner normally must hold a light source in one hand while using the other hand to hold and manipulate the tongue depressor against the patient's tongue.

U.S. Pat. No. 4,807,599 discloses an illuminating tongue depressor which avoids the need for a separately held light source thereby allowing a one-hand operation for illuminated inspection of the particular area being examined. The tongue depressor includes a handle having a battery-operated light source and a depressor blade selectively coupled with or uncoupled from the handle for discard and replacement. The blade is constructed of a light-conducting synthetic resin material formed with a lateral arch along the axis of the blade to resist bending along the length thereof. The blade also includes a light-receiving surface at the proximal end thereof and a light-directing configuration at the distal end thereof for directing light conducted from the light source and projected from the distal end to a defined area to be inspected during use of the depressor in the examination of a patient. However, it has been found that, during use, as the depressor is pushed against the soft tissue of the patient's tongue, the light-directing configuration at the distal end becomes positioned in a recess of the tongue formed by the yielding of the tongue surface under the pressure of the depressor end. As a result, the light-directing configuration at the distal end is positioned slightly below the top surface of the tongue immediately adjacent the light-directing configuration. Consequently, the tongue portion in front of the distal end blocks the light emitted from the light-directing configuration thus interfering with the illumination of the area to be examined.

U.S. Pat. Nos. 4,344,419 and 4,996,976 disclose other forms of tongue depressors having a handle, a blade and an illuminating means attached to the blade for illuminating the region of a throat to be examined. These depressors include an illumination means, such as a lens or optical fibers, formed on the top surface of the blade to assist in directing the light. In both the '419 and the '976 references, the outermost portion of each blade, closest the area to be examined, is also used to transmit light. However, this outermost portion of the depressor is generally flat and, therefore, will often be positioned below the surface of the tongue preventing the effective utilization of the outermost illuminating edge of the blade.

U.S. Pat. No. 2,723,661 to Hull and U.S. Pat. No. 3,734,084 to Ousterhout disclose examples of conventional tongue depressors used to assist in the examination of a patient. The tongue depressor disclosed in the Hull patent includes a concave portion at one end which faces downwardly against the patient's tongue during use. The concave portion provides strength and rigidity to the depressor while conforming to the shape of the tongue thereby decreasing any slippage of the depressor. The tongue depressor disclosed in the Ousterhout patent includes a blade having a lower tongue-engaging surface including a longitudinally extending central groove for receiving an endotracheal tube. However, these tongue depressors do not include a light illuminating and directing portion to illuminate the particular area being examined. Therefore, these depressors require a separate additional light source and a means for effectively directing the light onto the inspection area of the patient.

Thus, there is a need for a simple and effective tongue depressor for providing sufficient tongue depression while simultaneously and effectively illuminating the particular area to be examined.

SUMMARY OF THE PRESENT INVENTION

It is one object of the present invention to provide an improved tongue depressor which combines the simplicity of a relatively thin tongue depressor having an overall configuration resembling the familiar wooded tongue depressors, with the economy and convenience of a synthetic resin material, and the advantages of an improved illuminating feature for directing projected light to the particular area to be examined.

Another object of the present invention is to provide an improved tongue depressor which avoids the blocking effect of the tongue in front of the depressor to provide improved illumination of the area to be examined.

Yet another object of the present invention is to provide an improved tongue depressor which permits one hand operation to attain illuminated inspection of the particular area of a patient's throat being examined.

A further object of the present invention is to provide an improved tongue depressor which is compact, portable and easy to use.

Yet another object of the present invention is to provide an improved tongue depressor which is simple in construction and inexpensive to manufacture in large numbers of consistent high quality.

A still further object of the present invention is to provide an improved tongue depressor having a blade portion which can be easily replaced after each use.

Another object of the present invention is to provide an improved illuminated tongue depressor having an illuminating configuration which is automatically activated and deactivated when the blade is installed into, and removed from the handle, respectively, thereby avoiding the separate steps of manually turning the light source on and off.

These and other objects of the present invention are achieved by providing an illuminated tongue depressor including a handle and a depressor blade for use in conjunction with the handle during inspection of a defined area of a patient's throat wherein the blade includes a length extending longitudinally between a proximal end and a distal end and laterally between opposite sides, and includes upper and lower surfaces, a peripheral edge between the upper and lower surfaces defining a relatively thin blade thickness, a root adjacent the proximal end of the blade, a tip at the distal end of the blade, and a light conducting material between the upper and lower surfaces and extending along the blade from the root to at least a portion of the peripheral edge at the tip of the blade. A light source is positioned adjacent the root of the blade for transmitting light to the light-conducting material which, in turn, conducts the light at least to the portion of the peripheral edge at the tip of the blade. A light directing configuration formed on the distal end directs the light transmitted by the light conducting material toward the defined area and includes a groove formed in the lower surface of the blade tip, an elevated portion of the peripheral edge formed opposite the groove at the tip and a support leg on both sides of the groove extending from the elevated portion for contacting the patient's tongue during use. The handle may include a switch having a movable arm which is moved by the blade when the blade is moved into a coupled position to place the light source in an energized mode thereby providing illumination.

BRIEF DESCRIPTION OF THE DRAWINGS

FIG. 3 is a top longitudinal cross-sectional view of the tongue depressor in an inverted position showing internal components;

FIG. 4 is a side longitudinal cross-sectional view taken along plane 4—4 of FIG. 1;

FIG. 5 is a lateral cross-sectional view take along plane 5—5 of FIG. 1;

FIG. 6 is a perspective view of the coupling device of the present invention removed from the handle;

FIG. 7 is a front elevational view of the tongue depressor of FIG. 1;

FIG. 8 is a partial, top elevational view of the one-piece upper housing of the present invention with the internal components removed;

FIG. 9 is a perspective view of a second embodiment blade of the present invention in its operative position.

DETAILED DESCRIPTION OF THE INVENTION

Throughout this application, the words "downward" and "upward" will correspond to the directions, respectively, toward and away from the patient's tongue when the tongue depressor of the present invention is in use in its operative position. The words "upper" and "lower" will refer to the portion of the tongue depressor which are, respectively, farthest away and closest to the patient's tongue when the tongue depressor is in use in its operative position.

Figure 1:
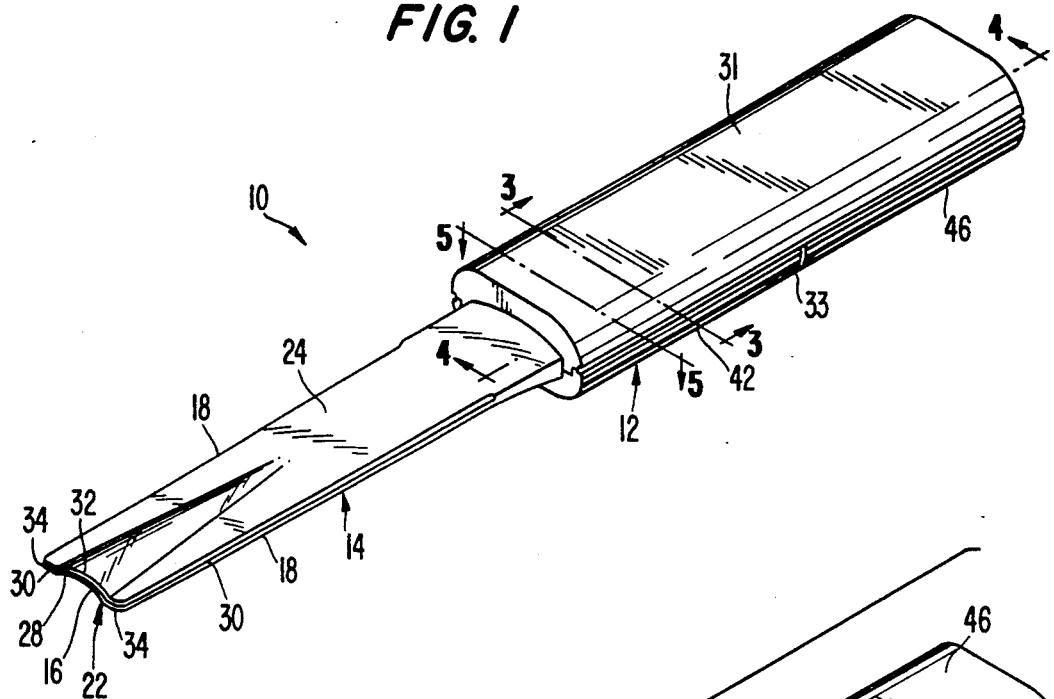
FIG. 1 is a perspective view of an illuminated tongue depressor constructed in accordance with the present invention in its operative position.
Figure 2:
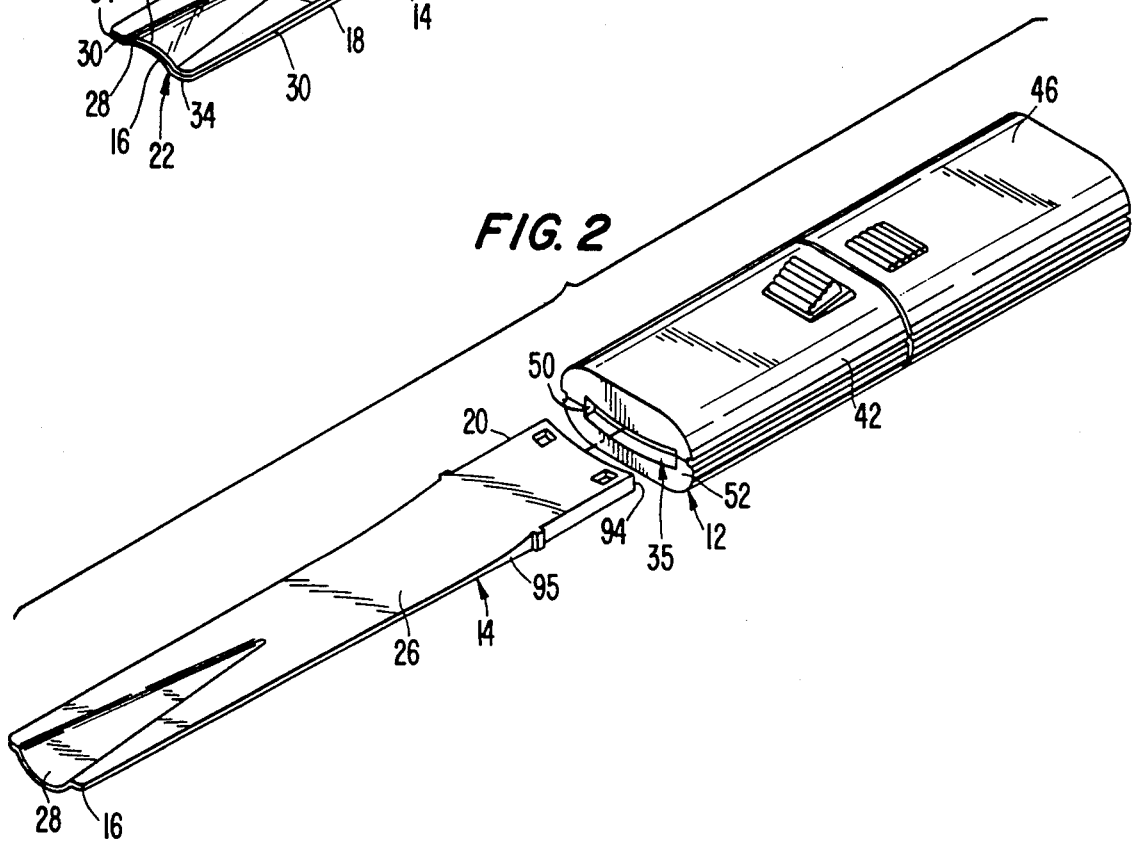
FIG. 2 is a perspective view of the illuminated tongue depressor of the present invention in an inverted position with the blade in the uncoupled position.

Referring to FIG. 1, an illuminated tongue depressor constructed in accordance with the present invention is illustrated in its operative position at 10 and includes a handle 12 and a depressor blade 14 projecting in a longitudinal direction from handle 12. Blade 14 includes a tip 16 formed at the distal end thereof, generally straight parallel sides 18, a root 20 (FIG. 2) formed at a proximal end relative to the handle, a uniform thickness along the length projecting beyond handle 12 and a light-directing configuration 22 formed on tip 16. Blade 14 is constructed of any light-conducting synthetic resin material, and may be molded from a clear acrylic, such as methacrylate, or styrene, for example, so as to be capable of conducting light along the length of the blade 14. Root 20 of blade 14 is secured at its proximal end within the handle in a coupled position adjacent a source of illumination so as to provide light to be conducted to tip 16 and directed by light directing configuration 22 toward the particular area to be examined with the aid of the tongue depressor 10. Blade 14 may also be released from handle 12 into an uncoupled position as illustrated in FIG. 2 in the inverted position.

Blade 14 also includes an upper surface 24 and a lower surface 26 which are arched in the lateral direction along the entire length of blade 14. FIG. 1 illustrates the tongue depressor 10 in its operative position wherein lower surface 26 is concave downwardly toward the patient's tongue during use. Tongue depressor 10 is generally used by grasping handle 12 and inserting blade 14 into the mouth of the patient. Tip 16 of blade 14 is manipulated to depress the tongue so a better view of the throat portion of the patient can be viewed. At the same time, light is emitted from the source of illumination in handle 12 and transmitted through blade 14 to light-directing configuration 22. Light-directing configuration 22 projects the transmitted light above the portion of the tongue tissue immediately in front of tip 16 and onto the area to be inspected. Also, some light is emitted from sides 18 of the blade to assist in inspecting further surrounding areas, such as the buccal and palatine areas of the oral cavity.

Light-directing configuration 22 includes a groove 28 formed in lower surface 26 of tip 16. Groove 28 is centrally positioned between sides 18 and extends longitudinally along blade 14 from tip 16 toward root 20 terminating at a point along the longitudinal axis of the blade between tip 16 and root 20. Groove 28 is laterally arched across the blade so that the lower surface of groove 28 is concave downwardly toward the patient's tongue when in use. The groove 28 continually and symmetrically diverges from its termination point to its widest point at a peripheral edge 30 of tip 16. In this manner, groove 28 forms an elevated portion 32 opposite groove 28 on upper surface 24 which includes a portion of peripheral edge 30. A support leg 34 is positioned on each side of groove 28 and elevated portion 32 for contacting the patient's tongue during use. Each leg 34 extends laterally from elevated portion 32 toward a respective side 18 in a plane generally parallel to the transverse plane of blade 14. Elevated portion 32, therefore, is positioned above legs 34 so that the portion of the peripheral edge 30 formed on elevated portion 32 is raised above the general plane of blade 14.

Referring to FIGS. 2-7, handle 12 includes a one-piece upper housing 31 connected to a lower housing 33 to form a cavity 35. A wall 36 extending downwardly from upper housing 31 and laterally across handle 12, divides cavity 35 into a coupling chamber 38 and a battery chamber 40. Lower housing 33 includes a coupling cover 42 connected to the upper housing 31 below coupling chamber 38 by a set of interlocking grooves 44 extending the length of handle 12. Lower housing 33 also includes a battery cover 46 connected to upper housing 31 by interlocking grooves 44 to form battery chamber 40 for receiving a set of batteries 48. Handle 12, including upper housing 31 and lower housing 33, is preferably constructed of a molded synthetic resin, such as polystyrene.

Handle 12 includes a socket 50 formed in an end wall 52 of upper housing 31 and coupling cover 42. Socket 50 is generally complementarily-shaped to the curvature of root 20 of blade 14 for receiving root 20 therein. The arched configuration of blade 14 along root 20 and the complementary socket 50 assures that blade 14 can be inserted into handle 12 only in the proper orientation, that is, with upper surface 24 facing upwardly and lower surface 26 facing downwardly.

As best shown in FIGS. 4 and 6, a coupling device, indicated generally at 54 in FIG. 6, permits the blade to be selectively coupled and uncoupled from handle 12 so that an expended blade can be discarded and replaced with a fresh blade. It should be noted that FIG. 6 illustrates coupling device 54 in an inverted position with respect to the operative position shown in FIG. 4. Coupling device 54 includes a generally Y-shaped, cantilevered spring 56 connected to coupling cover 42 by a screw 58. Spring 56 extends towards battery chamber 40 and includes two upwardly extending protrusions 60 formed laterally opposite one another. Coupling device 54 also includes two notches 62 formed in the lower surface of root 20 and positioned laterally opposite one another. Notches 62 are spaced a lateral distance across root 20 equal to the lateral spacing of protrusions 60 such that when root 20 is inserted into socket 50 protrusions 60 are aligned to engage notches 62. Thus, blade 14 is automatically coupled to handle 12 by pushing root 20 into socket 50 a sufficient distance to allow protrusions 60 to engage notches 62.

Coupling device 54 further includes a pivot plate 64 which includes an arm 65 extending laterally across pivot plate 64. The ends of arm 65 are each rotatably positioned in a complementary recess 66 (FIG. 8), formed on each side of upper housing 31 for allowing pivot plates 64 to pivot around a lateral axis passing through arm 65. Pivot plate 64 includes a pair of extensions 67 positioned laterally opposite one another on one side of the lateral axis adjacent spring 56 for moving protrusions 60 of spring 56 out of notches 62 to assist in moving blade 14 from the coupled position to the uncoupled position. A pair of inclined ramps 68 each formed on pivot plate 64 directly above one of the extensions 67 also assist in moving the blade 14 to an uncoupled position. As shown in FIG. 4, when pivot plate 64 is rotated about arm 65 in a clockwise direction, inclined ramps 68 are forced downwardly against the upper peripheral edge of root 20 imparting an outwardly directed longitudinal force on blade 14 forcing the blade out of socket 50. A stop shoulder 70 formed adjacent each of the ramps 68 is engaged by the proximal end of the blade 14 when root 20 is seated properly in socket 50. A button 72 is formed on pivot plate 64 on a side opposite extensions 67 and ramps 68 such that arm 65 is positioned between button 72 and extensions 67 and ramps 68. Button 72 extends through an opening 74 formed in coupling cover 42 to allow the user of the tongue depressor to operate coupling device 54. Thus, uncoupling of blade 14 from handle 12 is simply accomplished by pushing button 72 causing pivot plate 64 to rotate about arm 65 forcing extensions 67 and ramps 68 to move downwardly uncoupling root 20 from coupling device 54.

Referring to FIGS. 3, 4 and 5, a light source in the form of a light bulb 76, preferably a krypton bulb, is positioned at one end in a channel 78 extending downwardly from the inner upper surface of upper housing 31. Channel 78 is formed in chamber 38 so as to position bulb 76 immediately adjacent the proximal end of root 20 when blade 14 is in the coupled position. Light bulb 76 is powered by batteries 48 contained within battery chamber 40, the batteries 48 being connected in series through a common contact 80. As best shown in FIG. 8, a first contact 82 is positioned in chamber 38 so as to contact at one end bulb 76. Contact 82 also extends into battery chamber 40 to contact a first battery terminal 84. A second contact 86 cradles bulb 76 and extends toward socket 50 along one side of coupling chamber 38 to form a movable arm 88. A third contact 90 is positioned along one side of upper housing 30 adjacent movable arm 88 at one end and extends to contact a second battery terminal 92 at a second end (FIG. 3). Movable arm 88 is normally biased away from third contact 90 when blade 14 is in the uncoupled position. As root 20 of blade 14 is inserted into socket 50, the outer peripheral edge of root 20 deflects arm 88 against third contact 90 to complete a circuit and illuminate light bulb 76. Consequently, movable arm 88 and third contact 90 form a switch which is automatically closed energizing bulb 76 when blade 14 is moved into the coupled position, and automatically opened de-energizing bulb 76 when blade 14 is moved to the uncoupled position.

Light bulb 76 is juxtaposed with the proximal end of the blade 14 so that light from light bulb 76 is transmitted to the material of blade 14. As explained above, blade 14 is constructed of a light-conducting material, such as clear acrylic, and the light transmitted to root 20 of blade 14 is conducted longitudinally along the length of blade 14 to the distal end thereof. In order to enhance the transmission of light to blade 14, root 20 is made thicker than the remainder of blade 14, thereby providing a larger area along a rear surface 94 of root 20 for gathering a greater amount of light from light bulb 76, while maintaining a thinner, more economical and readily usable portion of blade 14 beyond root 20.

In view of the compact nature of handle 12, the intensity of the light available from bulb 76 and batteries 48 is limited. Yet it is important to direct the maximum amount of light available to the particular area to be inspected in connection with examination of a patient with tongue depressor 10. As set forth above, root 20 is made thicker in order to enable more light to be gathered at rear surface 94 of root 20. Thus, as best seen in FIG. 2, the height or altitudinal extent, of rear surface 94 preferably is about the same as the diameter, or altitudinal extent, of light bulb 76. The transition between the thicker and thinner portions of blade 14 is made smooth and continuous as shown at 95, so as to avoid loss of light along the transition. The light impinging on rear surface 94 will be conducted along the length of blade 14 to the distal end thereof. The upper surface 24 and lower surface 26 of blade 14 preferably are made smooth and uninterrupted so as to enhance total internal reflection and minimize any loss of light through the surfaces. In this manner, maximum use is made of the limited amount of light available as a result of the compact nature of handle 12.

Referring to FIG. 9, a second embodiment of light-directing configuration 22 is shown. In addition to groove 28, elevated portion 32 and support legs 34, tip 16 of blade 14 is provided with a graduated profile for effectively directing the light available at peripheral edge 30 so that the projected light will be concentrated and directed to the particular defined area to be illuminated for inspection. The graduated profile includes a step 96 proceeding upwardly from lower surface 26 and inwardly from peripheral edge 30 to form a land 98 facing upwardly toward upper surface 24 of blade 14. Step 96 extends along peripheral edge 30 at tip 16 and continues along each side 18 of blade 14. Step 96 preferably has a lenticular cross-sectional shape in order to effect appropriate directing of the light projected into the areas to be inspected. Additional steps may be formed on the peripheral edge of blade 14 to change the light-directing characteristics of blade 14.

In order to use the tongue depressor of the present invention, root 20 of blade 14 is inserted into socket 50 in the proper orientation as shown in FIG. 1. As root 20 passes through socket 50, the proximal end of root 20 will force spring 56 downwardly until protrusions 60 engage notches 62. In this coupled position, the proximal end of root 20 abuts stop shoulders 70 of pivot plate 64. Also, simultaneous with the insertion of blade 14, the outer edge of root 20 contacts movable arm 88 deflecting arm 88 outwardly into contact with third contact 90 closing the circuit and energizing bulb 76. Therefore, when blade 14 has been fully inserted into socket 50 of handle 12, the blade is automatically securely coupled to handle 12 and the source of illumination, that is light bulb 76, is automatically energized, thereby transmitting light to light-directing configuration 22 for projection onto the area to be examined. At the completion of the examination, blade 14 is removed for disposal or sterilization by pushing button 72 inwardly into opening 74 which causes pivot plate 64 to pivot about arm 65. As a result of this pivoting action, inclined ramps 68 and extensions 67 are moved toward spring 56. Extensions 67 force protrusions 60 of spring 56 to disengage notches 62. At the same time, inclined ramps 68 impart an outwardly directed longitudinal force on root 20 which tends to push blade 14 out of chamber 38 through socket 50 into an uncoupled position.

In most instances, a different blade 14 will be used for each patient and uncoupled from handle 12 after each use for disposal or resterilization. Therefore, since the illuminating qualities of the tongue depressor are needed substantially the entire time a blade is coupled to handle 12, the automatic switch 89 avoids the additional step of manually energizing and deenergizing light bulb 76. Moreover, once tip 16 of blade 14 is pressed against the surface of the tongue, support legs 34 maintain elevated portion 32 above the portion of the tongue immediately in front of tip 16 thereby allowing the light projecting from the peripheral edge of elevated portion 32 to be directed onto the area of the patient's throat to be examined.

I claim:

1. An illuminated tongue depressor for directing light to a defined area beyond the surface of a tongue to assist in the inspection of the defined area, the tongue depressor comprising:

a handle;

a depressor blade for use in conjunction with the handle during inspection of the defined area, the blade having a length extending longitudinally between a proximal end and a distal end and laterally between opposite sides, and including upper and lower surfaces, a peripheral edge between the upper and lower surfaces defining a relatively thin blade thickness, a root adjacent the proximal end of the blade, a tip at the distal end of the blade, and a light-conducting material between the upper and lower surfaces and extending along the blade from the root to at least a portion of the peripheral edge at the tip;

a source of illumination including a light source associated with the handle and located so as to juxtapose the light source adjacent the root of the blade for transmitting light to the light-conducting material, which light-conducting material, in turn, will conduct the light at least to the portion of the peripheral edge at the tip of the blade; and a light-directing means formed on said distal end for directing the light transmitted by said light-conducting material toward the defined area, said light-directing means including an elevated portion of said peripheral edge at said tip of said distal end and first and second support legs laterally extending from said elevated portion at said tip of said distal end, said first and second support legs extending from said elevated portion to said peripheral edge terminating in a plane generally parallel to a transverse plane of said blade to maintain said elevated portion above the surface of the tongue.

2. The illuminated tongue depressor of claim 1, further including a groove formed in the lower surface of said tip of said distal end, opposite said elevated portion wherein said first support leg is positioned on a first side of said groove and said second support leg is positioned on a second side of said groove laterally opposite said first side.

3. The illuminated tongue depressor of claim 2, wherein said groove extends along a central, longitudinal axis of said blade between said opposite sides and at least a portion of said groove is arched in the lateral direction.

4. The illuminated tongue depressor of claim 3, wherein at least an additional portion of the blade between the root and the tip is arched in the lateral direction having a first radius of curvature.

5. The illuminated tongue depressor of claim 4, wherein said groove includes a second radius of curvature, said first radius of curvature being greater than said second radius of curvature of said groove.

6. The illuminated tongue depressor of claim 1, wherein said first and said second support legs include a portion of said peripheral edge at said tip of said distal end.

7. The illuminated tongue depressor of claim 1, wherein said light directing means further includes a graduated profile configuration extending along the portion of the peripheral edge at the tip of the blade for directing projected light from the portion of the peripheral edge at the tip of the blade toward the defined area, the graduated profile configuration including at least one step extending along the portion of the peripheral edge of the tip.

8. The illuminated tongue depressor of claim 7, wherein said graduated profile configuration extends along substantially the entire peripheral edge of the blade.

9. The illuminated tongue depressor of claim 8, wherein said graduated profile configuration includes a plurality of steps which are arranged to form a plurality of lands facing upwardly toward said upper surface of the blade.

10. The illuminated tongue depressor of claim 1, wherein the blade is constructed of a light-conducting synthetic resin material.

11. The illuminated tongue depressor of claim 10, wherein the root of the blade includes a light-receiving surface confronting the light source, the light source has a given altitudinal extent at the light-receiving surface, the thickness of the blade between the upper and lower surfaces at the light-receiving surface being greater than the thickness of the blade between the upper and lower surfaces at the tip such that the altitudinal extent of the light-receiving surface essentially matches the altitudinal extent of the light source.

12. The illuminated tongue depressor of claim 1, further including coupling means for selectively coupling and uncoupling the blade and the handle.

13. The illuminated tongue depressor of claim 12, wherein:
   the coupling means includes a socket in the handle for receiving the root of the blade;
   the blade, including the root thereof, is arched in the lateral direction such that the upper surface is convex and the lower surface is concave; and
   the socket is arched complementary to the root of the blade for receiving the root only in the orientation where the upper surface faces upwardly and the lower surface faces downwardly.

14. An illuminated tongue depressor for directing light to a defined area to assist in the inspection of the defined area, the tongue depressor comprising:
   a handle;
   a depressor blade for use in conjunction with the handle during inspection of the defined area, the blade having a length extending longitudinally between a proximal end and a distal end and laterally between opposite sides, and including upper and lower surfaces, a peripheral edge between the upper and lower surfaces defining a relatively thin blade thickness, a root adjacent the proximal end of the blade, a tip at the distal end of the blade, and a light-conducting material between the upper and lower surfaces and extending along the blade from the root to as least a portion of the peripheral edge at the tip;
   a source of illumination including a light source associated with the handle and located so as to juxtapose the light source adjacent the root of the blade for transmitting light to the light-conducting material, which light-conducting material, in turn, will conduct the light at least to the portion of the peripheral edge at the tip of the blade, said light source capable of being operated in an energized mode providing illumination and a de-energized mode; and
   a coupling means for selectively coupling and uncoupling the blade and the handle, said blade movable between a coupled position in which said blade is connected to said handle and an uncoupled position in which said blade is disconnected from said handle, said coupling means including a socket formed in the handle for receiving the root of the blade, said root of the blade positioned adjacent said light source when said blade is in said coupled position, wherein said light source is automatically placed in said energized mode when said blade is moved into said coupled position, said coupling means including:
   one or more notches formed in said root;
   a biasing spring attached to said handle, said biasing spring including one or more protrusions adapted to engage said one or more notches when said blade is in said coupled position;
   a pivot plate positioned in said socket adjacent said light source, said pivot plate pivotable about a lateral axis and including one or more extensions positioned adjacent said biasing spring on a first side of said lateral axis;
   a button positioned on a second side of said lateral axis opposite said first side, said button being operable to pivot said pivot plate about said lateral axis to move said one or more extensions against said biasing spring to cause said one or more protrusions to disengage said one or more notches.

15. The illuminated tongue depressor of claim 14, further including a switching means for switching said light source between said energized mode and said de-energized mode, said switching means including a movable arm positioned adjacent said coupling means, said root adapted to move said movable arm when said blade is moved into said coupled position to place said light source in said energized mode.

16. The illuminated tongue depressor of claim 14, wherein said coupling means further includes one or more inclined ramps positioned on said first side of said lateral axis, said biasing means biasing said root against said one or more inclined ramps and said button operable to force said one or more inclined ramps against said root to force said blade into said uncoupled position.

* * * * *